United States Patent [19]

Raitto

[11] 4,215,701
[45] Aug. 5, 1980

[54] ELASTOMERIC PLUNGER TIP FOR A SYRINGE

[75] Inventor: Russell G. Raitto, Fitzwilliam, N.H.

[73] Assignee: Concord Laboratories, Inc., Keene, N.H.

[21] Appl. No.: 935,304

[22] Filed: Aug. 21, 1978

Related U.S. Application Data

[63] Continuation-in-part of Ser. No. 870,118, Jan. 17, 1978, which is a continuation-in-part of Ser. No. 714,644, Aug. 16, 1976, abandoned.

[51] Int. Cl.² ............................................. A61B 5/00
[52] U.S. Cl. ................................. 128/763; 128/218 P
[58] Field of Search ......... 128/218 P, 218 PA, 218 R, 128/215, 234, 220, 221, 760, 763

[56] References Cited

U.S. PATENT DOCUMENTS

| 786,697 | 4/1905 | Wackenhuth | 128/218 P |
|---|---|---|---|
| 1,948,982 | 2/1934 | Cutter | 128/218 P |
| 2,419,401 | 4/1947 | Hinds | 128/218 P |
| 2,766,754 | 10/1956 | Hill | 128/218 P |
| 3,147,753 | 9/1964 | Nogier et al. | 128/218 P |
| 3,662,753 | 5/1972 | Tassell | 128/218 M |
| 3,890,956 | 6/1975 | Moorehead | 128/2 F |
| 4,057,052 | 11/1977 | Kaufman et al. | 128/218 P |

FOREIGN PATENT DOCUMENTS

| 2025379 | 12/1971 | Fed. Rep. of Germany | 128/218 P |
|---|---|---|---|
| 2261631 | 6/1974 | Fed. Rep. of Germany | 128/218 P |
| 1228933 | 4/1902 | France | 128/218 P |

Primary Examiner—John D. Yasko
Attorney, Agent, or Firm—Sewall P. Bronstein; George W. Neuner

[57] ABSTRACT

An elastomeric plunger tip for syringes comprises a compressible, elastomeric material having a durometer of about 35 to about 75 when measured on the Shore A scale and maintains its resilience at temperatures at least as low as 0° C. The plunger tip is provided with a peripheral annular wiper lip extending axially forwardly and radially outwardly into sealing contact with the syringe barrel.

44 Claims, 8 Drawing Figures

ELASTOMERIC PLUNGER TIP FOR A SYRINGE

This application is a continuation-in-part of my co-pending application Ser. No. 870,118 filed Jan. 17, 1978 which is a continuation-in-part of application Ser. No. 714,644 filed Aug. 16, 1976 now abandoned.

BACKGROUND OF THE INVENTION

This invention relates generally to a hypodermic syringe for obtaining a sample of a body fluid, more particularly for drawing samples from the patient's artery or vein for blood gas analysis or other testing, and for administering fluids, more particularly for administering epidural anaesthesia.

Various syringes and method for taking blood samples from patients are known. Such samples are normally taken by means of a syringe which includes a generally cylindrical syringe barrel having a plunger therein which, when pulled axially by an operator, creates a suction force drawing blood into the barrel through a hypodermic needle. Many tests are performed on the blood which is thus obtained from the vein of the patient. However, an increasingly important method of determining the medical status of a patient is the obtaining of arterial blood samples for testing the blood for its content of various gases. Such samples are tested for the partial pressure of oxygen, the partial pressure of carbon dioxide, the pH of the blood, the electrolyte balance, and various other tests known in the art.

Syringes previously used in obtaining arterial blood samples have generally been glass syringes, in which the cylindrical barrel is made of glass and the plunger is a ground glass rod which closely fits within the cylinder. Generally the technique for taking samples with such devices comprises, as a first step, the drawing of an anticoagulant solution, such as sodium heparin, into the syringe to replace the air in the syringe. This solution also acts as a lubricant for the walls so that the glass plunger may move relatively freely within the cylinder. The syringe is inverted and all air is expelled from the barrel and needle, along with the bulk of the anticoagulant solution, which is normally far in excess of the amount needed for the blood sample. It is extremely important that all air be expelled from the syringe, since one of the tests performed is the measurement of the amount of oxygen present in the blood, and even minute contamination with air will prevent accurate measurement of that amount. After suitable preparation of the patient, the hypodermic needle is inserted into the artery and blood is either forced into the syringe by the pressure of the blood in the artery or is drawn into the syringe barrel by withdrawing the plunger. One advantage of the glass syringe previously used is the ease with which the plunger may be moved within the lubricated barrel. The glass plunger is ground to very close tolerances, so that it is sufficiently close to the syringe barrel wall to prevent leakage but sufficiently far away to allow formation of a thin film of the anticoagulant. Even very low arterial blood pressures are usually sufficient to enter the syringe and force the glass plunger backwards without any aid from the person taking the sample. Upon entry into the syringe the blood mixes with whatever anticoagulant solution remains in the needle, syringe tip and syringe barrel after the excess has been expelled.

Glass syringes are also conventionally used in epidural anaesthesia employing the loss of resistance technique because of the low resistance to movement of the plunger in the barrel. Such technique involves loading the syringe with 2-3 ml of normal saline, sterile distilled water or air. The needle (usually 16-18 g) is then applied to the syringe. The needle is then inserted into the back towards the spinal area in question, all the while exerting gentle pressure on the plunger. When the needle tip goes through the ligamenta flava into the potential epidural space, the loss of resistance will be immediately felt by the thumb because the fluid or air will be pushed into the space. Thereafter the syringe is removed from the inserted needle and is replaced on the needle by a syringe loaded with anaesthesia. This "loss of resistance" technique requires a syringe with an exceedingly smooth action and low resistance.

The glass syringes previously used have suffered from a number of disadvantages. They are expensive since the grinding requires close tolerances, in the order of 0.0007 inches clearance between the piston and the cylindrical syringe body. They are easily breakable, which is especially costly after the sample has been taken. The glass plunger and the glass barrel of each syringe must commonly be matched during the grinding by the manufacturer, since variations in grinding from one plunger to another may be sufficient to permit leakage of air or other material around the plunger, which will contaminate the sample. Thus the barrels and plungers cannot easily be individually mass produced since the plungers often cannot be satisfactorily interchanged one with another in any given barrel, as pointed out in U.S. Pat. No. 2,419,201 to Hinds. Further, because of the easy movement of the glass plunger in the cylinder, the plunger falls out of the barrel of its own weight, and normally breaks on the floor unless the syringe is carried needle end down. Special metal holders for the glass barrel have been used to prevent this problem.

Attempts have been made to avoid these disadvantages by either manufacturing both the barrel and the plunger out of materials other than glass, such as plastics, or by using glass barrels with plastic plungers. In order to prevent leakage around the plunger, these syringes depend upon the use of a compressible and elastomeric tip at the end of the plunger, which tip generally has one or more ribs which are slightly larger in diameter than the inside of the barrel in their uncompressed state and which, when placed within the barrel, are deformed and compressed against the interior will of the barrel and thereby form a seal. This type of seal, however, has made the movement of the plunger within the barrel difficult, thus normally requiring manual withdrawal of the plunger to obtain the blood sample, particularly when the patient's arterial pressure is low as is often the case. The handling of the syringe which is involved when manual withdrawal of the plunger is required may cause traumatization or collapse of the artery from which the blood is being taken.

SUMMARY OF THE INVENTION

This invention provides a compressible elastomeric plunger tip for a syringe and a syringe comprising such a plunger tip. The plunger tip is made from an elastomeric material having a durometer in the range of from about 35 to about 75 when measured on the Shore A scale. The elastomeric plunger tip is provided with a peripheral annular wiper lip extending axially forwardly and radially outwardly so that when attached to a plunger and inserted into a syringe barrel, the peripheral annular wiper lip extending axially forwardly toward the floor of the syringe barrel and radially outwardly at an acute angle to the longitudinal center line of the barrel and plunger. The normal outer diameter of the wiper, i.e., the wiper edge, is slightly greater than the inner diameter of the syringe barrel. By virtue of the fact that the wiper extends at an acute angle to the longitudinal center line of the barrel and plunger it tends to be forced to rock radially inwardly about its base (where it is joined to the main part of the plunger tip) against the resilient resistance offered by the elastomeric material when forced into the syringe barrel, whereby the wiper edge is yieldably pressed against the inner wall of the barrel to form an effective seal therebetween which increases in effect with increase in the force tending to move the plunger axially.

The elastomeric material is selected so that it maintains its resilience at temperatures of at least as low as 0° C. and preferably at temperatures as low as −40° C. Suitable materials for the practice of this invention include, for example, natural rubber and its man-made equivalents, butyl rubbers, silicone rubbers, and the like.

Although the seal achieved is excellent, the wiper edge is only lightly pressed against the barrel surface so that the plunger responds to lower pressures as compared to conventional plastic syringes. Accordingly, the syringe fills automatically by even very low arterial pressures with no need for manually withdrawing the plunger and is very sensitive to the touch which makes it highly satisfactory for epidural anaesthesia employing the loss of resistance technique.

THE DRAWINGS

DETAILED DESCRIPTION OF THE INVENTION

In accord with the present invention, a compressible elastomeric plunger tip comprises an elastomeric material having a durometer in the range of about 35 to about 75, preferably in the range of about 50 to 70 when measured on the Shore A scale and the material maintains its resilience at temperatures at least as low as 0° C., and preferably as low as −40° C. Any suitable elastomeric material having the above properties can be used in the practice of this invention. Typical examples of suitable materials include natural rubbers and their man-made equivalents, butyl rubbers including brominated and chlorinated butyl rubbers, silicone rubbers, and the like. A particularly useful material is natural gum rubber having a durometer of about 63. An example of a material not falling within the present invention is neoprene.

The elastomeric plunger tip in accord with this invention is provided with a peripheral annular wiper lip extending axially forwardly and radially outwardly to provide the sole sealing contact with a syringe barrel when in use.

Syringes comprising the elastomeric plunger tips of this invention provide excellent sealing in spite of the very low pressure required to fill the syringes. This seal is maintained even when the drawn blood sample in the syringe is placed in ice immediately after the sample is drawn. In preferred embodiments of this invention, the seal is maintained even at temperatures as low as about −40° C. that may be encountered when shipping syringes in refrigerated trucks. Maintaining the seal during shipment is very important in the case of syringes that are prefilled with an anticoagulant such as heparin. Using a material having a durometer selected in the aforesaid range provides minimum resistance to axial movement of the plunger tip in the syringes of this invention.

Figure 1:
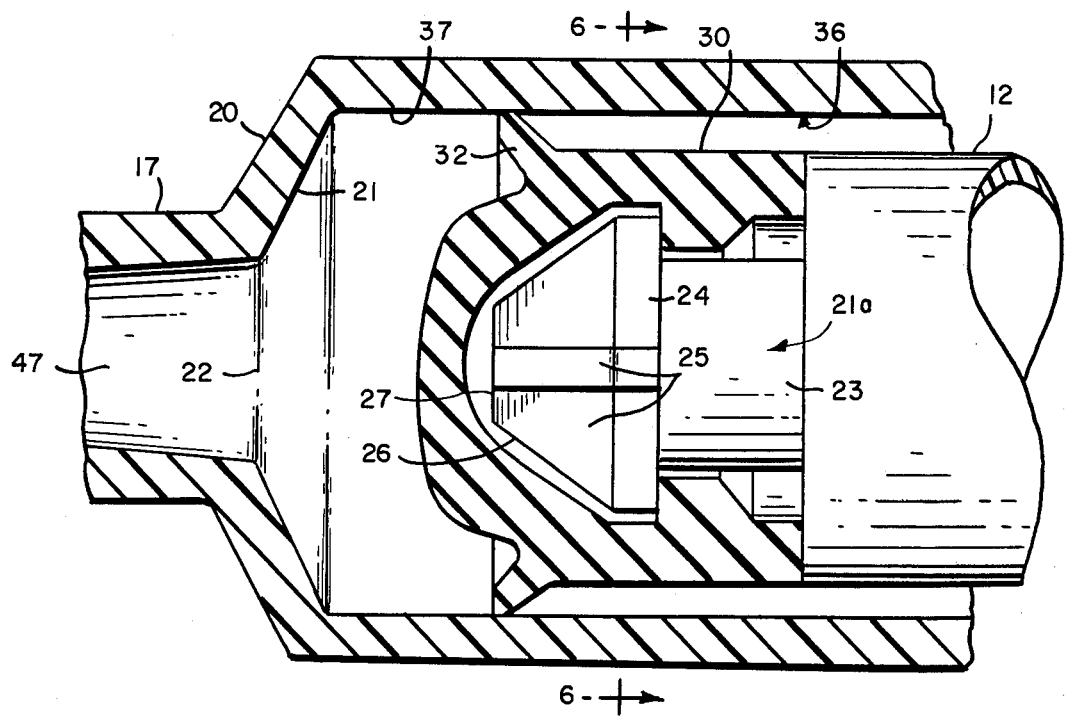
FIG. 1 is a sectional view of the forward portion of a syringe having an elastomeric plunger tip in accord with a preferred embodiment of this invention.
Figure 2:
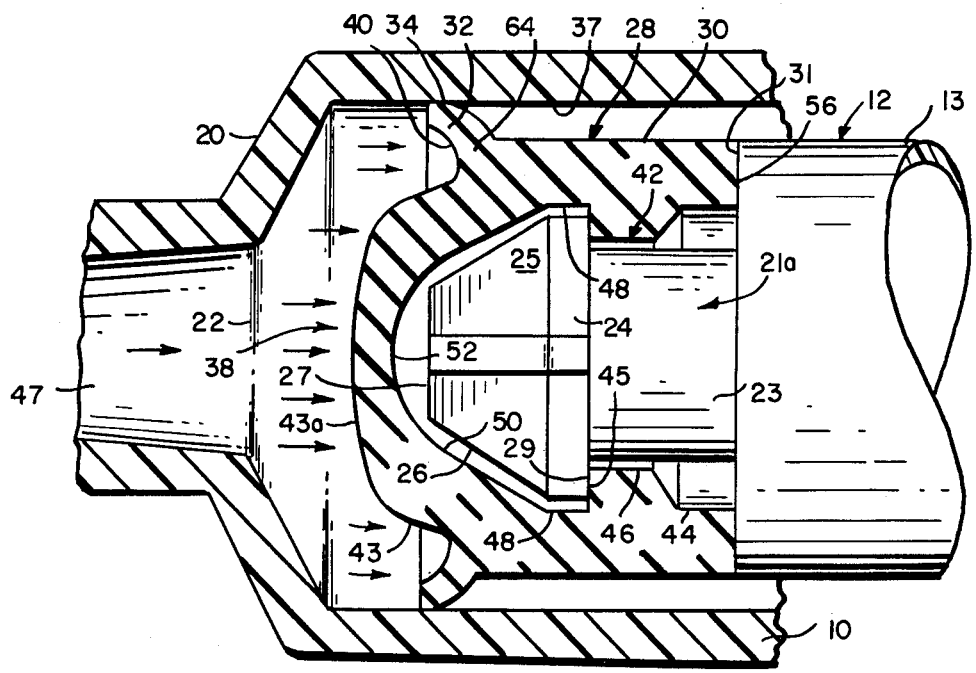
FIG. 2 is a view like FIG. 1 showing how force applied to the tip forces the wiper edge tighter against the barrel wall to increase sealing effect.
Figure 3:
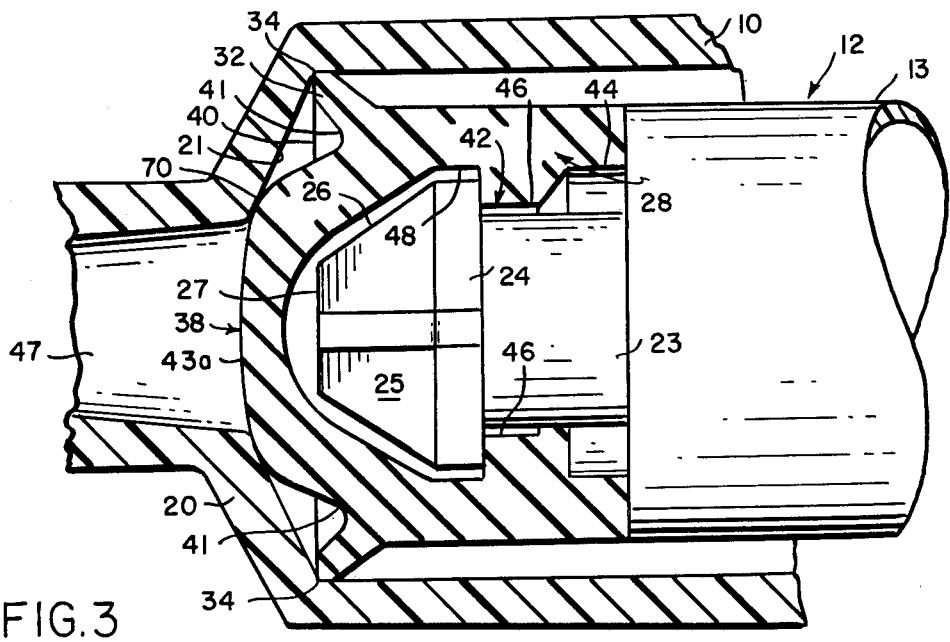
FIG. 3 is a view like FIG. 1, showing the initial contact position of the plunger tip and barrel floor wherein the needle opening is sealed.
Figure 4:
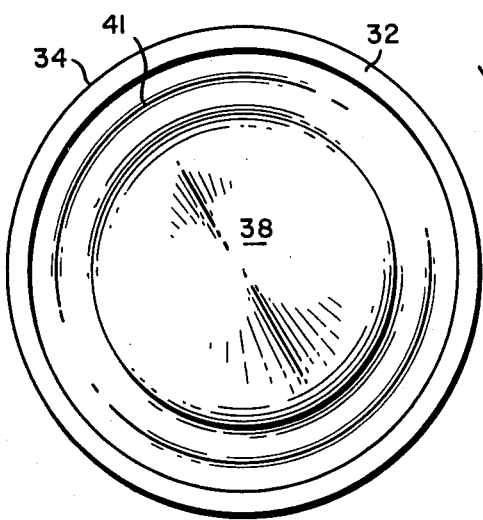
FIG. 4 is an inner end view of the plunger tip of FIG. 1.
Figure 5:
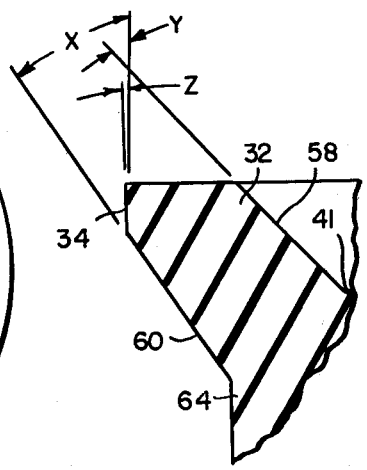
FIG. 5 is an enlarged view in section of a part (rotated so that the longitudinal axis is oriented vertically in the illustration) of the wiper of the plunger tip of FIG. 4 before it is inserted into the syringe barrel.

Referring to the drawings, in a preferred embodiment of this invention a hollow compressible and elastomeric plunger tip 28 is made up of main hollow cylindrical portion 30 from the periphery of the forward portion of which extends axially forwardly (axially forwardly and axially inwardly mean toward the barrel floor whereas axially rearwardly and axially outwardly mean away from the barrel floor) and radially outwardly at an acute angle y see FIGS. 2, 3 and 5) from the longitudinal center axis of the plunger and plunger tip, an annular wiper lip 32, the wiping edge 34 of which is resiliently and yieldably forced into sealing engagement with the inner bore or wall 37 of the barrel. The plunger tip extends axially forwardly from the base 64 of wiper 32 into a reduced diameter leading end portion 38, the base 43 of which has an outside frusto-conical shaped taper which terminates in a convex curvilinear end face 43a. An annular recess or trough 41 is formed by the axially forward and radially inner surface 58 of the annular wiper 32 and the radially outer surface 43 of the end portion 38, as shown.

The rearward end 56 of plunger tip 28 has an internal socket 42 in which is received the head 21a of the plunger stem 12 to secure the plunger tip to the end of the plunger stem. Socket 42 has an enlarged rear cylindrical end portion 44 which extends forwardly into a reduced cylindrical portion 46 which then extends forwardly into an enlarged diameter cylindrical portion 48 (same diameter as 44) which forms a shoulder 29 where it meets with portion 46 and which extends forwardly into a radially inwardly tapered frusto-conical shaped portion 52. The taper of socket wall 50 is slightly sharper than that of outer surface 43 and the curve of socket wall 52 is slightly sharper than that of outer surface 43a, as shown.

Preferably, the circle formed where the frusto-conical outer surface 43 of end portion 38 changes into the curvilinear end surface 43a, lies on an imaginary axial extension of cylindrical socket walls 48 and 44.

The cylindrical portion 23 of the head 21a of the plunger stem is located within the rearward portions 44 and 46 of the plunger tip socket and is spaced radially inwardly therefrom as shown. The square shaped plate portion 24 of the plunger stem is located within the enlarged cylindrical portion 48 of the plunger tip socket and is spaced radially inwardly therefrom as shown. The fins 25 of the plunger stem head are located within the tapered portion 50 of the socket and are spaced radially inwardly therefrom and the ends thereof are spaced axially rearward from the end wall 52 of the socket, all as shown. The annular end 56 of the plunger tip is held in secure engagement with the shoulder 31 of the plunger stem and the shoulder 29 of the socket is held in secure engagement with the shoulder 45 of the plunger stem head to thereby firmly secure the plunger tip on the end of the plunger stem 13.

The only part of the plunger which engages the inner wall of the barrel is the annular wiping edge 34 which exerts only a slight force on such wall to thereby reduce frictional drag and permit the plunger to be easily moved axially in the barrel.

The acute angle y between the forward or leading wiper surface 58 (FIG. 5) of the wiper 32 and the longitudinal center axis of the plunger tip is slightly greater han the acute angle x between the rearward or trailing wiper surface 60 of the wiper and the longitudinal center axis whereby the wiper is tapered in thickness with the base 64 of the wiper being thicker than the end portion of the wiper. The thickner base strengthens the wiper whereas the tapered thinner end portion increases the flexibility of the wiper edge to provide only gentle sealing pressure on the inner barrel wall to thereby minimize resistance to axial movement of the plunger.

In its relaxed state when the plunger tip is removed from the barrel, the wiper edge 34 of the wiper is of slightly greater diameter than the inner bore 37 of the barrel so that when the plunger tip is forced into the bore such edge 34 is forced radially inwardly about the base 64 of the wiper i.e., the wiper is bent or rocked radially inwardly about its base, against the force exerted by the elastic and compressible material, which force yieldably and with only a slight pressure urges such wiper edge into excellent sealing engagement with the bore wall 37 with very little fractional drag.

In its relaxed state when the plunger tip is removed from the barrel, the wiper edge surface 34 preferably extends radially outwardly and axially forwardly at a slight angle z, e.g., about 2° to the longitudinal center axis of the plunger tip and the barrel bore. The purpose of this is to reduce the chance of leakage while still achieving gentle sealing pressure. When the plunger tip is forced into the barrel bore, this wiper edge surface 34 is forced to assume a position in which it is parallel to the longitudinal axis of the plunger tip and barrel bore. Without this slight inclination of the wiper edge surface 34, the undersized barrel may tend to bend the leading end of such wiper edge surface radially inwardly to either reduce the pressure of the wiper edge surface on the bore wall at such leading end or to cause such leading end to move slightly away from the bore wall to provide a slight space or groove therebetween which may result in leakage. The force of the liquid blood sample shown by the arrows in FIG. 2 tends to aggravate this since it tends to work into any space or decreased pressure area between such leading end and the barrel bore to force such leading end further away from the bore wall with resulting leakage.

By providing this slight angle to the wiper edge surface 34, maximum sealing pressure is applied and concentrated at the leading end of surface 34 where it does the most good and over a relatively small area, thereby minimizing frictional drag.

As aforesaid, the plunger tip can be made of any elastomeric and compressible material that keeps its resilience at low temperatures and can be made in the proper durometer. Preferably the material also has memory, a low coefficient of friction with the barrel wall material and is inert to the sample material, to the anticoagulant and to any other substance which is to be located within the syringe barrel.

It will be noted that the forward end of the plunger tip is so designed that when the plunger tip is moved to its forwardmost position as shown in FIG. 3, the inital contact of the plunger tip with the barrel floor is between the narrow annular area 70 of the barrel floor 21 immediately adjacent the needle opening 22 and the peripheral part of the curved end surface 43a of the end portion 38 of the plunger tip to thereby seal the needle opening 22 against further flow of fluid out of the syringe through the needle opening. At this time the wiper edge 34 reaches the end of the cylindrical bore wall 37 and the trough 41 of the wiper forms with the barrel floor 21 a sealed space or chamber 40 of predetermined size, i.e., sealed by the seal between the plunger tip and the barrel floor at 70 and the seal between the tip and the barrel bore at 34. Note that the difference in taper of the outer and inner surfaces 43 and 50 of the plunger tip increases the wall thickness of the tip behind the seal area 70.

Conventionally in taking a blood sample, a liquid anticoagulant, e.g., sodium heparin, to prevent coagulation of the blood sample is either drawn into the syringe before the blood sample is taken or is located in the syringe as packaged. The excess of such liquid anticoagulant and any air in the syringe is then expelled through the needle opening and needle by forward movement of the plunger and plunger tip.

Figure 6:
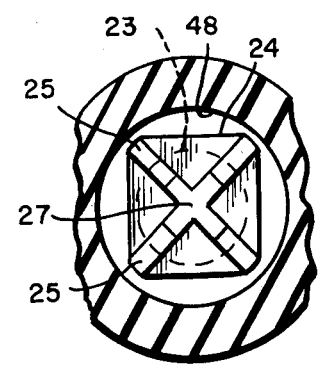
FIG. 6 is a section taken along the line 6—6 of FIG. 1.

The excess anticoagulant and air are expelled by moving the plunger tip to its forwardmost position as shown in FIG. 3. The initial sealing contact between the narrow annular area 70 of the barrel floor immediately adjacent the needle opening and the convex end surface 43a of end portion 38 seals the syringe barrel against further flow of the liquid anticoagulant out of the syringe and a predetermined amount of the anticoagulant is thereby trapped in the annular space 40. The size of the trough 41 is such that the amount of anticoagulant trapped in this space, together with that filling passage 47 and the needle when the plunger tip is in the position shown in FIG. 6, is sufficient to prevent coagulation of the sample taken but is less than an amount which will interfere with the testing of the sample. Accordingly, the right amount of anticoagulant is automatically assured.

Preferably the volume of the space 40, together with passage 47 and the needle bore, is between 0.01 and 1.0 milliliters and more preferably between 0.25 and 0.5 milliliters for every 5 milliliter of blood sample taken.

Although the design of the wiper tip assures that a predetermined volume of anticoagulant is left in the syringe, due to the compressibility of the plunger tip, air can be drawn into the needle after expelling excess anticoagulant. To prevent this, it may be desirable to include a stop for limiting the forward motion of the plunger tip and the subsequent drawing of air into the needle.

In spite of the very low pressure required to fill the syringe of the invention and the very gentle sealing pressure of the wiper edge against the syringe barrel, the sealing achieved is excellent by virtue of the design of the wiper in accord with this invention. As seen in FIG. 2, the force shown by the arrows applied by the blood pressure tends to urge the wiping edge against the barrel wall to increase the sealing effect. The plunger tip of the invention has withstood a hydraulic force of 300 mm/Hg without leaking but such large forces are not encountered in use.

The optimum angle y of the wiper from the longitudinal center axis of the plunger tip and optimum angle z of the wiper edge surface and optimum difference in the angles y and x of the leading and trailing surfaces of the wiper to achieve a thin wiper edge portion and a thicker base depends in part upon the stiffness of the material of the plunger tip.

It has been found that an angle y of 43°, (preferably it varies between about 20° and 65°, more preferably between about 30° and 50°) between the leading surface of the wiper and the longitudinal axis of the plunger tip and an angle x of 135° (preferably the difference over angle y may vary between about 10° and 30°, more preferably between about 4° and 15°) between the trailing surface and the longitudinal axis gives excellent results.

Excellent results have also been achieved with needle sizes of from 20 to 22 gage. The speed with which the plunger tip moves is proportional to the needle gage size.

It has been found that air bubbles which in conventional plastic syringes collect at the leading surface of the plunger tip close to the interface of the plunger tip and the barrel bore, do not collect on such surface of the plunger tip of this invention. It is believed that this is due to the particular design of the plunger tip. This is an important advantage since it permits more accurate testing.

The location of the liquid-containing space 40 axially in front of substantially the entire solid axial length of the wall of the plunger tip to which the force is axially applied at 56 greatly strengthens the plunger tip. This is achieved in part by reducing the diameter of the end portion 38 as compared to the main portion of the plunger tip. Although such reduction in diameter strengthens the wiper, it, together with the radially inward taper at 43a, reduces wiper stiffness and thereby increases wiper sensitivity and reduces frictional drag.

Figure 7:
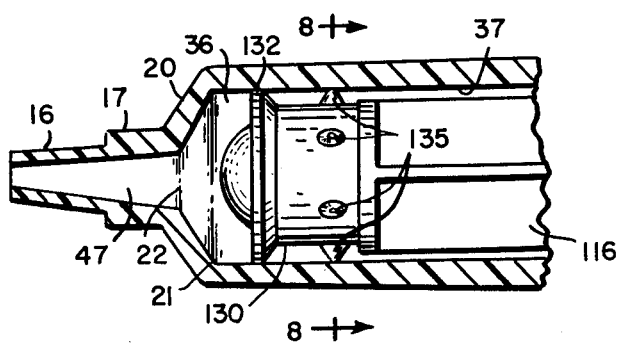
FIG. 7 is a side view of a partial longitudinal section of a preferred embodiment of the syringe of the present invention.
Figure 8:
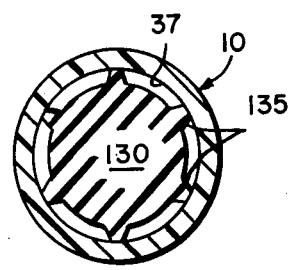
FIG. 8 is a section taken along line 8—8 of FIG. 7.

In another preferred embodiment as illustrated in FIG. 7, the elastomeric plunger tip 130 has a plurality of raised portions 135 spaced around the circumference of the rearward section of the plunger tip 130 and engaging the inner wall 37 with minimum contact to avoid any significant frictional force. These raised portions 135 of the plunger tip 130 prevent canting of the plunger tip to maintain the plunger tip in a concentric position within the syringe barrel 10 and allow the sole wiping edge 132 of the plunger tip to maintain its most effective sealing engagement with the syringe barrel. The raised portions on the rear section of the plunger tip can be of any shape that will accomplish the purpose of preventing canting of the plunger tip. Generally, a semi-spherical, conical, or frusto-conical shape is preferred to avoid excessive frictional contact with the syringe barrel and for ease of manufacture.

Syringes embodying elastomeric plunger tips of this invention are highly useful as improved arterial blood sampling syringes and also for epidural anesthesia employing the loss of resistance technique and they have been used successfully clinically for that purpose.

In a preferred embodiment, syringes having elastomeric plunger tips in accord with this invention are prefilled with an anticoagulant such as, for instance, heparin. Thus, the need to draw up anticoagulant prior to taking a blood sample from a patient is eliminated.

It is not intended that the invention be limited to or by the aforesaid description and accompanying drawings of only one embodiment thereof but only to the subject matter claimed hereinafter and its equivalents.

What is claimed is:

1. An elastomeric plunger tip particularly suited for a blood sampling syringe, said tip comprising a compressible, elastomeric material having a durometer of about 35 to about 75 when measured on the Shore A scale, having the ability to retain its resilience at temperatures at least as low as 0° C., and being provided with a peripheral annular wiper lip extending axially forwardly and radially outwardly so that it forms the sole sealing element when said plunger tip if inserted in said syringe, said plunger tip providing the syringe with a self-aspirating characteristic when used to sample arterial blood while maintaining an effective seal for containing the blood sample.

2. An elastomeric plunger tip according to claim 1 wherein said material has a durometer of about 50 to 70 on the Shore A scale.

3. An elastomeric plunger tip according to claim 1 wherein said material is selected from the group consisting of natural rubber and its man-made equivalents, butyl rubbers and silicone rubbers.

4. An elastomeric plunger tip according to claim 1 wherein said material is natural gum rubber.

5. An elastomeric plunger tip according to claim 4 wherein said natural gum rubber has a durometer of about 63 on the Shore A scale.

6. An elastomeric plunger tip according to claim 1 wherein said material is butyl rubber.

7. An elastomeric plunger tip according to claim 1 wherein said material has the ability to retain its resilience at temperatures of about −40° C.

8. A compressible and elastomeric syringe plunger tip particularly suited for a blood sampling syringe comprising a generally cylindrical main portion, an integral annular elastically deformable wiper extending peripherally radially outwardly and axially forwardly from a forward portion thereof at an acute angle to the longitudinal center axis of said tip and terminating at the outer edge thereof in a wiping edge, when used in a syringe assembly said annular wiper being the sole sealing element between said plunger tip and the syringe, said tip comprising a compressible, elastomeric material having a durometer of about 35 to about 75 when measured on the Shore A scale, having the ability to retain its resilience at temperatures at least as low as 0° C., and being provided with a peripheral annular wiper lip extending axially forwardly and radially outwardly so that it forms the sole sealing element when said plunger tip is inserted in said syringe, said plunger tip providing the syringe with a self-aspirating characteristic when used to sample arterial blood while maintaining an effective seal for containing the blood sample.

9. A tip according to claim 8, said main portion having an end portion of reduced diameter.

10. A tip according to claim 9, said wiper and reduced diameter portion forming an annular trough in the forward face of said tip.

11. A tip according to claim 8, the edge of said wiper comprising a generally cylindrically shaped surface which extends radially outwardly and axially forwardly at a straight acute angle to the longitudinal center line of said tip.

12. A tip according to claim 11, the thickness of said wiper being tapered from the base thereof to the free end thereof so it is thicker at its base than at its end.

13. An elastomeric plunger tip according to claim 8 wherein said material has a durometer of about 50 to 70 on the Shore A scale.

14. An elastomeric plunger tip according to claim 8 wherein said material is selected from the group consisting of natural rubber and its man-made equivalents, butyl rubbers and silicone rubbers.

15. An elastomeric plunger tip according to claim 8 wherein said material is natural gum rubber.

16. An elastomeric plunger tip according to claim 15 wherein said natural gum rubber has a durometer of about 63 on the Shore A scale.

17. An elastomeric plunger tip according to claim 8 wherein said material is silicone rubber.

18. An elastomeric plunger tip according to claim 8 wherein said material has the ability to retain its resilience at temperatures of about −40° C.

19. A tip according to claim 8, the thickness of said wiper being tapered from the base thereof to the free end thereof so that it is thicker at its base than at its end.

20. A syringe assembly according to claim 19, wherein the angle between the leading surface of said wiper and the longitudinal axis is between about 30° and 50° and the angle of the taper is between about 10° and 15°.

21. A syringe assembly according to claim 8, said wiping edge comprising a plane surface of minor dimension oriented substantially parallel to the longitudinal axis of said plunger tip.

22. A syringe assembly according to claim 21 wherein said plane surface extends radially outwardly and axially forwardly at a very slight angle.

23. A syringe assembly according to claim 22 wherein the angle is about 2°.

24. A compressible and elastomeric syringe plunger tip comprising a generally cylindrical main portion, an integral annular elastically deformable wiper extending peripherally radially outwardly and axially forwardly from a forward portion thereof at an acute angle to the longitudinal center axis of said tip and terminating at the outer edge thereof in a wiping edge, when used in a syringe assembly said annular wiper being the sole sealing element between said plunger tip and the syringe, said tip comprising a compressible, elastomeric material having a durometer of about 35 to about 75 when measured on the Shore A scale, having the ability to retain its resilience at temperatures at least as low as 0° C., and being provided with a peripheral annular wiper lip extending axially forwardly and radially outwardly so that it forms the sole sealing element when said plunger tip is inserted in said syringe, said plunger tip having a plurality of raised portions speed circumferentially around said plunger tip and located at the rearward portion of said plunger tip, said raised portions engaging the wall of said syringe, when the plunger tip is inserted therein, to prevent canting of said plunger tip.

25. An elastomeric plunger tip according to claim 24 wherein said material has a durometer of about 50 to 70 on the Shore A scale.

26. An elastomeric plunger tip according to claim 24 wherein said material is selected from the group consisting of natural rubber and its man-made equivalents, butyl rubbers and silicone rubbers.

27. An elastomeric plunger tip according to claim 24 wherein said material is natural gum rubber.

28. An elastomeric plunger tip according to claim 27 wherein said natural gum rubber has a durometer of about 63 on the Shore A scale.

29. A self-aspirating disposable syringe assembly particularly suited because of the low force requirement for the operation thereof to be used for obtaining a blood sample from a patient comprising a barrel having a cylindrical inner wall and a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the other edge thereof in a wiping edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall, said plunger tip comprising a compressible, elastomeric material having a durometer of about 35 to about 75 when measured on the Shore A scale, having the ability to retain its resilience at temperatures at least as low as 0° C., and being provided with a peripheral annular wiper lip extending axially forwardly and radially outwardly so that it forms the sole sealing element when said plunger tip is inserted in said syringe, said plunger tip providing the syringe with a self-aspirating characteristic when used to sample arterial blood while maintaining an effective seal for containing the blood sample.

30. A syringe assembly according to claim 29, said wiper being tapered from the base thereof to the free end thereof so that it is thicker at its base than at its end.

31. A syringe assembly according to claim 30, wherein the angle between the leading surface of said wiper and the longitudinal axis is between about 30° and 50° and the angle of the taper is between about 10° and 15°.

32. A disposable syringe assembly according to claim 29 wherein said material has a durometer of about 50 to 70 on the Shore A scale.

33. A disposable syringe assembly according to claim 29 wherein said material is selected from the group consisting of natural rubber and its man-made equivalents, butyl rubbers and silicone rubbers.

34. A disposable syringe assembly according to claim 29 wherein said material is natural gum rubber.

35. A disposable syringe assembly according to claim 34 wherein said natural gum rubber has a durometer of about 63 on the Shore A scale.

36. A syringe assembly according to claim 29, said wiping edge comprising a plane surface of minor dimension oriented substantially parallel to the longitudinal axis of said plunger tip.

37. A syringe assembly according to claim 36 wherein said plane surface extends radially outwardly and axially forwardly at a very slight angle.

38. A syringe assembly according to claim 37 wherein the angle is about 2°.

39. A syringe according to claim 29, including a hypodermic needle secured to said barrel for insertion into the artery of a patient to withdraw a blood sample from said patient, the frictional force of said sealing engagement being of a mangitude that allows the blood pressure of said patient to move said plunger stem and tip backwardly in said barrel to draw said blood sample from said patient into said barrel.

40. A disposable syringe assembly particularly suited because of the low force requirement for the operation thereof to be used for obtaining a blood sample from a patient comprising a barrel having a cylindrical inner wall and a plunger comprising a plunger stem and a compressible, elastomeric, generally cylindrical plunger tip of lesser diameter than the inner wall of said barrel, said plunger tip having an integral, annular, elastically deformable wiper extending peripherally radially outwardly and axially forwardly from said plunger tip at a forward portion thereof at an acute angle to the longitudinal center axis of said plunger tip and terminating at the outer edge thereof in a wiping edge having a minimal diameter slightly in excess of the diameter of the inner wall of said barrel, thereby forming a sealing engagement with the inner wall of said barrel, said annular wiper being the sole sealing element between said plunger tip and said wall, said plunger tip having a plurality of raised portions spaced circumferentially around said plunger tip and located at the rearward portion of said plunger tip, said raised portions engaging said inner wall of said barrel with a minimum of frictional contact to prevent canting of said plunger tip in said barrel, said plunger tip comprising a compressible, elastomeric material having a durometer of about 35 to 75 when measured on the Shore A scale, having the ability to retain its resilience at temperatures at least as low as 0° C., and being provided with a peripheral annular wiper lip extending axially forwardly and radially outwardly so that it forms the sole sealing element when said plunger tip is inserted in said syringe, said syringe assembly being prefilled with anticoagulant.

41. An elastomeric plunger tip according to claim 40 wherein said material has a durometer of about 50 to 70 on the Shore A scale.

42. An elastomeric plunger tip according to claim 40 wherein said material is natural gum rubber.

43. An elastomeric plunger tip according to claim 42 wherein said natural gum rubber has a durometer of about 63 on the Shore A scale.

44. An elastomeric plunger tip according to claim 40 wherein said material has the ability to retain its resilience at temperatures of about −40° C.

* * * * *

UNITED STATES PATENT AND TRADEMARK OFFICE
CERTIFICATE OF CORRECTION

PATENT NO. : 4,215,701
DATED : August 5, 1980
INVENTOR(S) : Russell G. Raitto

It is certified that error appears in the above-identified patent and that said Letters Patent are hereby corrected as shown below:

Col. 1, line 16, change "method" to ---methods---.

Col. 2, line 50, change "will" to ---wall---.

Col. 4, line 36, before "see" insert ---(--- (a parenthesis).

Col. 5, line 24, change "han" to ---than---.

line 28, change "thickner" to ---thicker---.

Claim 1, Col. 8, line 23, change "if" to ---is---.

Claim 24, Col. 9, line 64, "speed" should be ---spaced---.

Claim 29, Col. 10, line 27, delete "thereof in a wiping edge".

Claim 39, Col. 11, line 10, change "mangitude" to ---magnitude---.

Signed and Sealed this

Eighteenth Day of November 1980

[SEAL]

Attest:

Attesting Officer

SIDNEY A. DIAMOND

Commissioner of Patents and Trademarks